United States Patent [19]

Bacha et al.

[11] Patent Number: 4,468,382

[45] Date of Patent: Aug. 28, 1984

[54] POLYPEPTIDE-TOXIN HYBRID PROTEIN

[75] Inventors: Patricia Bacha, Brookline; Seymour Reichlin, Weston; John R. Murphy, Roslindale, all of Mass.

[73] Assignee: New England Medical Center, Inc., Boston, Mass.

[21] Appl. No.: 398,677

[22] Filed: Jul. 15, 1982

[51] Int. Cl.$^3$ ..................... A61K 37/00; C07C 103/52
[52] U.S. Cl. ............................... 424/177; 260/112.5 R
[58] Field of Search .................. 424/177; 260/112.5 R

[56] References Cited

U.S. PATENT DOCUMENTS 4,340,535  7/1982  Voisin et al. .................... 260/112 R

OTHER PUBLICATIONS

Miskimins et al., Biochem. Biophys. Res. Commun., vol. 91, pp. 143–151, (1979).
Cawley et al., Cell, vol. 22, pp. 563–570, (1980).
Miskimins et al., PNAS (USA), vol. 78, pp. 445–449, (1981).
Uchida et al., Nature, (New Biology), vol. 233, pp. 8–11, (1971).
Chang et al., J. Biol. Chem., vol. 252, pp. 1515–1522, (1977).
Oeltmann et al., J. Biol Chem., vol. 254, pp. 1028–1032, (1979).

Primary Examiner—Delbert R. Phillips

[57] ABSTRACT

A hybrid protein toxic to cells having linear neuropeptide receptors such as TRH receptors comprising a linear neuropeptide such as TRH covalently bonded to CRM 45 is useful for treatment of tumors.

6 Claims, No Drawings

POLYPEPTIDE-TOXIN HYBRID PROTEIN

This invention was made in the course of work supported by the U.S. Government, which has certain rights in the invention.

This invention relates to a class of hybrid proteins useful for therapeutic treatment of selected mammalian cells comprising linear neuropeptides coupled by a covalent disulfide-containing linkage to a toxin fragment and pertains more specifically to a hormone-toxin hybrid protein useful for therapeutic treatment of pituitary cells, as in pituitary tumors, and for clinical management of hypertension and muscle spasms of paraplegic patients. More specifically the invention relates to a chimera comprising thyrotropin releasing hormone (TRH) coupled to the toxin known as cross-reacting material 45 (CRM 45), the premature terminated tox gene product (m.w. 45,000 vs. m.w. 62,000 of native toxin) of the mutant $C.$ $diphtheriae$ strain $C_7(\beta$ tox-45) as described by Uchida et al., Nature (New Biology), Vol. 233, 8–11 (1971).

It has long been a goal to provide a therapeutic agent capable of damaging or destroying specific selected cells (the target cells) within an organism without affecting other cells. While hybrid proteins consisting of a toxin coupled to a ligand capable of binding specifically to a selected class of cells have previously been proposed, they have been ineffective as therapeutic agents for a variety of reasons. It has been proposed to synthesize a hybrid protein consisting of diphtheria toxin A chain coupled to human placental lactogen hormone by cross-linking through a disulfide bond. However, although the chimera did bind to cells containing lactogen receptors, it did not inhibit protein synthesis in those cells, as reported in Chang et al., J. Biol. Chem. Vol. 252, 1515–1522 (1977). A chimera consisting of ricin A toxin coupled to the $\beta$ chain of human chorionic gonadotropin hormone by similarly cross-linking through a disulfide bond has been reported; although said to have specifity, its binding capacity has not been reported and extremely high concentrations were required to significantly inhibit protein synthesis in rat Leydig tumor cells, making it extremely difficult to distinguish between "non-specific" entry due to endocytosis and "specific" entry due to transport of the toxic portion of the chimera across the cyloplasmic membrane of the target cells. Oeltman et al., J. Biol. Chem., Vol. 254, 1028–1032 (1979). The same shortcoming was found in a hybrid consisting of diphtheria A coupled to insulin using cystamine as the cross-linking agent. Miskimins et al., Biochem. Biophys. Res. Commun., Vol. 91, 143–151 (1979). A hybrid consisting of ricin A coupled to epidermal growth factor (EGF) by means of a heterobifunctional cross-linker has been made but the binding characteristics provided by the EGF are not limited to selected specific cells but encompass a wide variety of cell types. Cawley et al., Cell, Vol. 22, 583–570 (1980).

It has now been found that a hybrid protein or chimera comprising a linear neuropeptide coupled by a covalent disulfide-containing linkage to CRM 45 retains the binding specificity of the linear neuropeptide to a high degree while also retaining the enzymatic activity (which inhibits cell protein synthesis) and high therapeutic ratio of CRM 45. Moreover, the free CRM 45, lacking the ability to bind to toxin-membrane receptors, is virtually non-toxic to all mammalian cells; consequently, the CRM 45 after coupling is toxic only to those cells to which the selected linear neuropeptide binds. The native structure of the CRM 45 molecule contains a hydrophobic amino acid sequence which is believed to facilitate passage of the hybrid molecule through the lipid membrane of the cell to which it binds. Among the linear neuropeptides which can form a part of the hybrid proteins of the present invention are thyrotropin releasing hormone (TRH), somatostatin, leutinizing hormone-releasing hormone, leu-enkephalin, met-enkephalin, neurotensin, substance P, oxytocin, gastrin, corticotropin releasing factor, cholecystokinin, motilin, and bombesin. Of these, TRH is preferred because, since only a few cell types carry TRH receptors, the range of target cells for the hybrid TRH-CRM 45 is very limited, being confined almost exclusively to certain of those of the pituitary (those that produce thyroid stimulating hormone and prolactin) and to a lesser extent to certain of the neurons of the hypothalamus and certain cells of the testis. The hybrid TRH-CM 45 does not bind to other closely related cells such as the pituitary cells which produce luteinizing hormone. Consequently, this hybrid is useful in treatment of pituitary tumors, in particular prolactinomas, thyrotropinomas, and somatotropinomas; and in management of hypertension and muscle spasms of paraplegic patients because of the ability of the hybrid to bind specifically to those neurons which control motor function and autonomic nervous system activity, both of which carry TRH receptors. The other hybrid proteins of the present invention are useful in treatments requiring damaging or destroying those cells to which the selected neuropeptide of the chimera binds.

The invention consequently comprises a hybrid protein toxic to cells having linear neuropeptide receptors comprising a linear neuropeptide covalently bonded through a disulfide linkage to CRM 45. A specifically preferred product comprises a hybrid protein toxic to cells having TRH receptors comprising TRH covalently bonded through a disulfide linkage to CRM 45. In a preferred embodiment the covalent bonding is between the histidyl imidazole group of TRH and any reactive group of CRM 45; still more preferably the bonding is between the hystidyl imidazole group of TRH and an amino or amido group of CRM 45. The invention in addition comprises a therapeutic composition, toxic only to cells carrying linear neuropeptide receptors, specifically TRH receptors, comprising the hybrid protein together with a physiologically acceptable non-toxic carrier such as normal saline, as well as the method of inhibiting protein synthesis in cells carrying such receptors which comprises bringing into contact with the cells a hybrid protein comprising a linear neuropeptide such as TRH covalently bonded to CRM 45, for example by parenteral injection of the therapeutic composition.

The covalent bonding of the linear neuropeptide to the CRM 45 may be accomplished by any conventional procedure for coupling by covalent reaction selected functional groups of each molecule to each other through conventional cross-linking agents which include a disulfide linkage. Of particular value is indirect coupling through bifunctional cross-linkers which react with amino groups (of the CRM 45) on the one hand and with histidyl imidazole groups (of the TRH) on the other hand, in several stages.

The following examples will serve to illustrate the preparation of a hybrid protein or chimera in accordance with the present invention but is not intended to limit the scope of the invention.

EXAMPLE 1

TRH and CRM 45 were covalently bonded by a two-stage reaction. In the first stage the TRH and CRM 45 were each individually reacted with bifunctional cross-linking agents to form reactive derivatives, and in the second stage the reactive derivatives were reacted with each other to form a covalently bonded hybrid protein.

A bifunctional cross-linking reagent was prepared by a condensation reaction between iodoacetic acid and cystamine catalyzed by 1-ethyl-3(3-dimethylaminopropyl)-carbodiimide HCl (EDAC) in a manner similar to that described by Gilliland et al., Proc. Natl. Acad. Sci. USA, Vol. 75, 5319-23 (1978) and in accordance with the following equation:

$$ICH_2-COH +$$
$$NH_2-CH_2-CH_2-S-S-CH_2-CH_2-NH_2 \longrightarrow$$
$$ICH_2-C(=O)-NH_2-CH_2-CH_2-S-S-CH_2-CH_2-NH_2 + H_2O$$

The reactants (25 mg iodoacetate, 50 mg cystamine, and 25 mg EDAC in 5 ml distilled $H_2O$) were mixed at room temperature in the dark with the pH maintained at 4.7.

After 30 minutes, the pH was raised to 5.6 and 2 mg commercially available synthetic TRH were added. The carboxymethylation reaction with TRH was allowed to proceed for 6 hrs. in the dark with gentle shaking in accordance with the following equation:

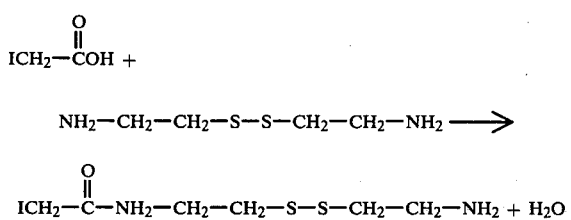

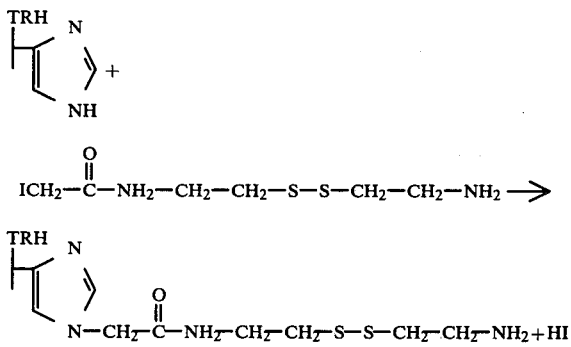

The fully derivatized acetylocystaminyl-TRH was purified on a Sephadex G-10 column equilibrated with phosphate buffered saline. Peak fractions were determined by optical density at 240 nm.

CRM 45 was purified by ammonium sulfate precipitation and DEAE ion-exchange chromatography as described in Bacha et al., J. Bacteriol., Vol. 136, 1135-1142 (1978) from culture supernatants of the lysogen $C_7$ ($\beta$tox-45) grown in deferrated CY medium. CRM 45 concentrations were determined by rocket immunoelectrophoresis, as described in Murphy et al., J. Clin. Microbiol., Vol. 7, 91–96 (1978).

Primary and secondary amino groups of the purified CRM 45 were derivatized with N-succimidyl-3 (2-pyridyldithio)-propionate (SPDP), which is a commercially available heterobifunctional cross-linker, in accordance with the following equation:

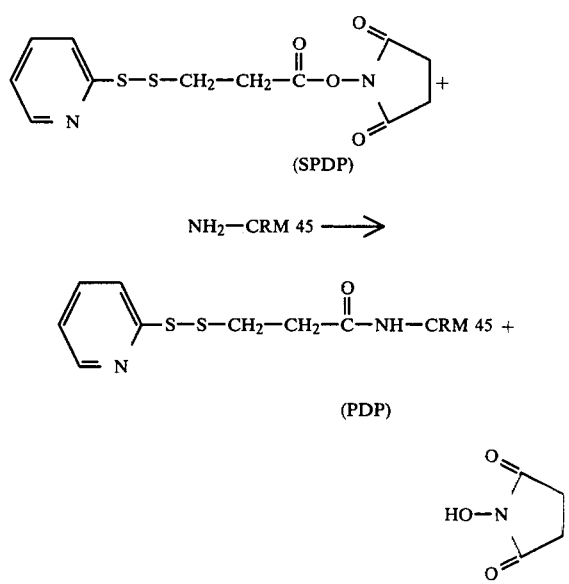

Briefly, CRM 45 (1 mg/ml) in 0.1M NaCl, 0.1M sodium phosphate buffer (pH 7.5) was mixed for 30 minutes at room temperature with a two-fold excess of SPDP dissolved in a small amount of absolute alcohol. The mixture was then dialyzed against 0.15M NaCl, 0.01M sodium phosphate (pH 7.5) (PBS). The degree of substitution was determined by the increase in absorbance at 343 nm after reduction of the 2-pyridyl disulfide (PDP) bond, as previously described by Stuchbury et al., Biochem. J., Vol. 151, 417–432 (1975). On the average there was 1 to 2 PDP residues per CRM 45 molecule. Such preparations retained ADPR-transferase activity when measured in vitro.

Covalent Bonding of TRH and CRM 45

Acetylcystaminyl-TRH prepared as described above was reduced with $5 \times 10^2$M dithiothreitol for 30 minutes at room temperature and then quickly desalted over a Sephadex G-10 column equilibrated with PBS. Fractions containing the modified TRH molecule with a free sulfhydryl group as determined by titration with 5,5'-dithiobis-(2-nitrobenzoic acid) and having the structure:

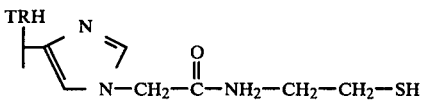

were immediately mixed with CRM 45-PDP in approximately a 10:1 mol ratio. The disulfide-reaction was allowed to proceed at room temperature and followed spectrophotometrically by the increase in absorbance at 343 nm. After the reaction was completed (usually 20 to 30 min), the mixture was dialyzed extensively against phosphate buffered saline to remove unreacted TRH molecules. The reaction produced a hybrid protein of the following structure:

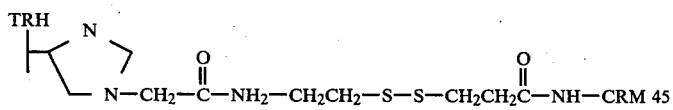

EXAMPLE 2

Fresh diazotized p-aminobenzoic acid was prepared by reacting 3.6 mg paminobenzoic acid in 100 μl 1N HCl on ice for 10 minutes with 1.8 mg $NaNO_2$ in 50 μl $H_2O$. A 15 μl aliquot was added to 500 μg TRH in 500 μl 1M NaCl, 0.1M borate buffer (pH 9.0). After 24 hours at 4° C., 6 mg cystamine, 5 mg 1-ethyl-3 (3-dimethylaminopropyl)-carbodiimide HCl, and 500 μl distilled $H_2O$ was added to the reaction mix. The pH was then adjusted to and maintained at 4.7 for 30 minutes. The fully derivatized TRH was purified over Sephadex G-10 equilibrated with phosphate buffered saline, and was then reduced with dithiothreitol, desalted, and reacted with CRM 45-PDP in the same manner as the acetylcystaminyl-TRH described in Example 1. The result was a hybrid protein of the following structure:

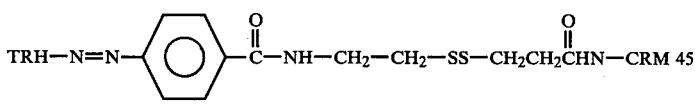

Determination of Specific Toxicity $GH_3$ rat pituitary tumor cells (Tashjian et al., 1968) were seeded in 24 well plates (Linbro) at a concentration of $5\times10^4$ cells per well in 0.5 ml Han's F10 medium supplemented with 15% horse serum, 2.5% fetal calf serum, and $2\times10^{-3M}$ glutamine. After 72 hours incubation, the medium was removed and the cells reincubated for an additional 24 hrs. with fresh medium containing the hybrid protein ($10^{-7}$ to $10^{-11}$M). The medium was then replaced with 0.25 μCi $^{14}$C-leucine (280 mCi/mml, New England Nuclear). After 1 hr., the medium was removed and the attached cells were washed extensively with 5% trichloroacetic acid. The cells were then solubilized in 0.5 ml Ultrafluor (National Diagnostics). Dose-response curves were constructed that compare the amount of leucine incorporated by intoxicated cultures as a percent of that incorporated by untreated control cultures.

Although the specific toxicity varied from batch to batch of the hybrid protein, typically a concentration of around $5\times10^{-9}$M of the hybrid protein of Example 1 caused a 50% inhibition of protein synthesis in this system, a toxicity approximately 200 to 500 times the toxicity of the original CRM 45 in the same system. The hybrid protein of Example 2 caused a 50% inhibition of protein synthesis in the same system at a concentration of $1\times10^{-8}$M.

Control experiments showed that the increased toxicity of the TRH-CRM 45 conjugate was intrinsic to the conjugate itself rather than due to the biochemical modifications of the components since acetylcystaminyl TRH was nontoxic in this system and CRM 45-PDP inhibited protein synthesis only to the same extent expected for CRM 45 alone. In addition, pretreatment of the conjugate with either $5\times10^{-2}$M dithiothietol (DTT) to break the disulfide cross-link or with diphtheria antitoxin abolished its toxicity. Also, intoxication of $GH_3$ cells by TRH-CRM 45 was prevented by a 1 hr. preincubation of the cells with excess TRH. Likewise, when the conjugate was tested on the 3T3 mouse fibroblast line which does not contain TRH receptors, it was no more toxic than CRM 45 alone.

The ability of the conjugate to compete with $^3$H-TRH for receptors on $GH_3$ cells was measured directy using the technique of Hinkle et al., J. Biol. Chem., Vol. 249, 3086-3090 (1974). It was clear that the hybrid protein of Example 1 ($K_A=3\times10^{-7}$) competes with the free TRH ($K_A=1\times10^{-8}$) for TRH receptor sites, although with a lower affinity, while the hybrid protein of Example 2 displayed an affinity constant $K_A=10^{-7}$M.

Localization studies done by gently radioiodinating either CRM 45 or the hybrid protein, chromatographically purifying, injecting into the tail vein of a rat, and decapitating after 15 minutes, showed increased uptake of the hybrid over CRM 45 in the anterior pituitary, hypothalamus and testis but not in the brain, liver, kidney, lung, or pancreas. An injection of excess non-radioactive CRM 45 at the same time as the labelled hybrid reduced absorption in the pituitary, hypothalamus, and testis tissues.

Basal secretion of TRH and prolactin by normal rat pituitary cells in culture was reduced by treatment with the hybrid protein, as compared to an untreated control. In addition, the amount of these two hormones released by TRH or high potassium pulse was also significantly lower in the treated cells. In contrast, LH secretion which is not regulated by TRH was unaffected in these cultures.

Treatment of lactating mother rats with the hybrid protein also inhibited prolactin production, causing death of the pups or failure to thrive.

What is claimed is:

1. A hybrid protein comprising TRH covalently bonded through a disulfide linkage to CRM 45.

2. A hybrid protein as claimed in claim 1 in which said bonding is between the histidyl imidazole group of said TRH and an amino group of said CRM 45.

3. The method of inhibiting protein synthesis in cells carrying TRH linear neuropeptide receptors which comprises bringing into contact with said cells a hybrid protein as claimed in claim 1.

4. A therapeutic composition toxic only to cells carrying receptors for TRH linear neuropeptide which comprises a hybrid protein as claimed in claim 1 together with a physiologically acceptable non-toxic carrier thereof.

5. The method as claimed in claim 3 in which said hybrid protein is bonded between the histidyl imidazole group of said TRH and an amino group of said CRM 45.

6. A therapeutic composition as claimed in claim 4 in which said hybrid protein is bonded between the histidyl imidazole group of said TRH and an amino group of said CRM45.

* * * * *